United States Patent [19]
Lin et al.

[11] Patent Number: 5,807,929
[45] Date of Patent: Sep. 15, 1998

[54] CYCLIC IMIDO-1,3,5-TRIAZINE CROSSLINKING AGENTS

[75] Inventors: Lon-Tang Wilson Lin, Bethel; Robert G. Lees, Stamford; William F. Jacobs, III, Bethel, all of Conn.; Subban Ramesh, Parsippany, N.J.

[73] Assignee: Cytec Technology Corp., Stamford, Conn.

[21] Appl. No.: 807,414

[22] Filed: Feb. 28, 1997

Related U.S. Application Data

[60] Provisional application No. 60/012,660 Mar. 1, 1996.

[51] Int. Cl.$^6$ .................. C08G 59/18; C09D 163/00; C08K 5/3492; C07D 403/14
[52] U.S. Cl. .................. 525/180; 528/170; 528/289; 528/310; 528/327; 528/331; 528/423; 525/181; 525/183; 525/408; 525/437; 525/444; 525/445; 525/534; 525/934; 544/194; 544/198; 544/204; 544/209; 544/212
[58] Field of Search .................. 528/170, 289, 528/310, 327, 331, 423; 525/180, 181, 183, 408, 437, 444, 445, 454, 534, 934; 544/194, 198, 204, 209, 212

[56] References Cited

U.S. PATENT DOCUMENTS

| | | | |
|---|---|---|---|
| 3,763,090 | 10/1973 | Cyba | 260/45.8 |
| 3,794,641 | 2/1974 | Gorog et al. | 260/249.8 |
| 4,064,191 | 12/1977 | Parekh | 260/850 |
| 4,081,426 | 3/1978 | Michel et al. | 260/67.6 |
| 4,101,520 | 7/1978 | Boldizar | 528/248 |
| 4,118,437 | 10/1978 | Parekh | 260/834 |
| 4,129,681 | 12/1978 | Anderson et al. | 428/524 |
| 4,226,989 | 10/1980 | DiLeone et al. | 544/198 |
| 4,243,705 | 1/1981 | Yapp et al. | 427/386 |
| 4,271,277 | 6/1981 | Golownia | 525/351 |
| 4,276,212 | 6/1981 | Khanna et al. | 260/39 R |
| 4,330,458 | 5/1982 | Spinelli et al. | 524/512 |
| 4,374,164 | 2/1983 | Blank | 427/385.5 |
| 4,425,466 | 1/1984 | Santer et al. | 524/512 |
| 4,433,143 | 2/1984 | Santer et al. | 544/196 |
| 4,873,298 | 10/1989 | Ryntz | 525/479 |
| 5,084,541 | 1/1992 | Jacobs, III et al. | 528/45 |
| 5,155,201 | 10/1992 | Gardon et al. | 528/78 |
| 5,256,713 | 10/1993 | Jacobs, III et al. | 524/99 |
| 5,288,865 | 2/1994 | Gupta | 544/200 |

FOREIGN PATENT DOCUMENTS

| | | |
|---|---|---|
| 0409334 A2 | 1/1991 | European Pat. Off. . |
| 0604922 A1 | 7/1994 | European Pat. Off. . |
| 0624577 A1 | 11/1994 | European Pat. Off. . |
| 0649842 A1 | 4/1995 | European Pat. Off. . |
| 0662504 A1 | 7/1995 | European Pat. Off. . |
| 112130 | 3/1975 | German Dem. Rep. . |
| 59672 | 2/1976 | Romania . |
| 89171 | 4/1986 | Romania . |
| WO 93/10117 | 5/1993 | WIPO . |
| WO 94/13664 | 6/1994 | WIPO . |
| WO 95/30663 | 11/1995 | WIPO . |
| WO 96/04258 | 2/1996 | WIPO . |
| WO 96/11915 | 4/1996 | WIPO . |
| WO 96/15185 | 5/1996 | WIPO . |
| WO 96/29318 | 9/1996 | WIPO . |
| WO 96/41826 | 12/1996 | WIPO . |
| WO 97/08235 | 3/1997 | WIPO . |

OTHER PUBLICATIONS

Chemical Abstracts 10420a, "Chloro–s–Triazines", Ichikawa et al., 1967.
International Search Report dated Aug. 4, 1997 (PCT/US97/03071).
Frommelt et al., "2–4–Bis(phthalimido)–s–triazines," Chemical Abstracts, vol. 84, No. 17, Apr. 26, 1976.

*Primary Examiner*—Frederick Krass
*Attorney, Agent, or Firm*—Pennie & Edmonds LLP

[57] ABSTRACT

At least bis-imido 1,3,5-triazines and processes of preparing the same are disclosed. Also disclosed are prepolymers having at least bis-imido functionality and curable compositions comprising at least bis-imido 1,3,5-triazines or prepolymers thereof in combination with active hydrogen and/or epoxy functional materials. The at least bis-imido 1,3,5-triazines and prepolymers may be advantageously employed as crosslinking agents which crosslink by a ring opening reaction that eliminates the release of volatile organic compounds.

41 Claims, No Drawings

CYCLIC IMIDO-1,3,5-TRIAZINE CROSSLINKING AGENTS

This application claims priority under 35 U.S.C. §119 from U.S. Provisional Application No. 60/012,660 (filed Mar. 1, 1996), which is incorporated by reference herein for all purposes as if fully set forth.

BACKGROUND OF THE INVENTION

1. Field of the Invention

The present invention relates generally to the use of polyfunctional (cyclic imido)-1,3,5-triazine compounds as crosslinking agents in curable compositions, and particularly powder coating compositions, as well as the preparation of novel prepolymers of such polyfunctional (cyclic imido)-1,3,5-triazine compounds which may also find use as crosslinking agents in curable compositions. The present invention also relates to certain of these polyfunctional (cyclic imido)-1,3,5-triazine compounds which in and of themselves are novel, as well as methods of preparing polyfunctional (cyclic imido)-1,3,5-triazines in general.

2. Description of Related Art

Various derivatives of amino compounds, such as amino-1,3,5-triazines and glycolurils, are described in the literature for use in a wide variety of fields. Certain of these derivatives, such as the partially or fully alkoxymethylated derivatives of melamine, guanamines and glycoluril, are useful as crosslinkers in curable compositions which contain resins having active hydrogen groups. See, for example, U.S. Pat. No. 4,064,191, U.S. Pat. No. 4,081,426, U.S. Pat. No. 4,101,520, U.S. Pat. No. 4,118,437, U.S. Pat. No. 4,129,681, U.S. Pat. No. 4,243,705, U.S. Pat. No. 4,271,277, U.S. Pat. No. 4,276,212, U.S. Pat. No. 4,330,458, U.S. Pat. No. 4,374,164, U.S. Pat. No. 4,433,143, U.S. Pat. No. 4,425,466, U.S. Pat. No. 4,873,298, U.S. Pat. No. 5,155,201, U.S. Pat. No. 5,256,713 and WO96/41826.

While these derivatives in general provide excellent results, they may release volatiles (including formaldehyde) during cure which is not desired. Thus, crosslinking agents with good performance characteristics and which minimize the release of volatiles during cure would be particularly advantageous and are highly desired.

One non-formaldehyde emitting alternative is the class of isocyanate and carbamate functional 1,3,5-triazine crosslinking agents disclosed in U.S. Pat. No. 4,939,213, U.S. Pat. No. 5,084,541, U.S. Pat. No. 5,288,865, EP-A-0604922, EP-A-0624577, EP-A-0649842, WO95/30663, WO96/04258, WO96/11915, WO96/15185, and U.S. application Ser. No. 06/002,950 (filed Aug. 30, 1995, now abandoned). Other non-formaldehyde emitting alternatives include, for example, the class of lactam substituted 1,3,5-triazine crosslinking agents disclosed in WO93/10117, and the class of acetal and enamine functional 1,3,5-triazine crosslinking agents disclosed in WO96/29318. The aforementioned have been found to be particularly useful as crosslinkers in coating compositions based on active hydrogen and/or epoxy groups containing resins, with the cured coatings possessing a wide range of desirable properties.

While some of these alternatives have shown great promise, the search continues for replacements for traditional amino derivative crosslinkers, which replacements retain many of the desirable properties of the traditional crosslinkers but which emit little or no volatiles on cure. As discussed in further detail below, the present inventors have found another such suitable replacement in polyfunctional (cyclic imido)-1,3,5-triazines.

Certain narrow classes of cyclic imido functional 1,3,5-triazines have been disclosed in the art. For example, U.S. Pat. No. 3,794,641 discloses mono- and polyfunctional phthalimido-1,3,5-triazines, which are stated to have herbicidal activity. The phthalimido-1,3,5-triazines are prepared by reacting cyanuric chloride with an alkali-metal phthalimide.

Romanian Patent No. 59672 and 89171 disclose polyfunctional maleimido-1,3,5-triazines, methods of preparing the same and uses thereof. Specifically, Romanian Patent No. 59672 discloses the use of such maleimido functional 1,3,5-triazines in the preparation of polyamine-polyimides by reacting these compounds in solution with aromatic diamines by Michael addition at the maleimide double bond. The resulting polyamine-polyamides are said to be useful in the preparation of fiber-reinforced laminates. Romanian Patent No. 89171 discloses a method of preparing such polyfunctional maleimido-1,3,5-triazines by reacting melamine and maleic anhydride in the presence of cyclohexanone as solvent and further in the presence of diphenylnitrosamine as a polymerization inhibitor.

WO94/13664 discloses mono(tetrahydrophthalo) melamine, which is stated to be a soluble melamine derivative useful as a reactive flame-retardant additive and as an intermediate in the preparation of other reactive flame-retardant additives.

Finally, EP-A-0409334 discloses mono(maleimido), mono(succinimido), mono(phthalimido) and another monofunctional 1,3,5-triazine, which are stated to be useful in the preparation of aromatic polymers with anisotropic behavior.

All of the above-mentioned references are hereby incorporated by reference herein for all purposes as if fully set forth.

None of these references, however, discloses or suggests the use of polyfunctional (cyclic imido)-1,3,5-triazines as crosslinking agents in powder coating compositions, prepolymers of these polyfunctional (cyclic imido)-1,3,5-triazines, the methods of making these compounds nor the various species of polyfunctional (cyclic imido)-1,3,5-triazines, in accordance with the present invention as described in further detail below and as set forth in the present claims.

SUMMARY OF THE INVENTION

In accordance with one aspect of the present invention, there is provided a curable composition, and preferably a curable, film-forming powder coating composition, which comprises, in its overall concept:

(i) a resin component (a solid resin component in the case of a powder coating) comprising a polyfunctional resin containing functional moieties selected from active hydrogen groups and epoxy groups; and (ii) a crosslinker component comprising a polyfunctional compound containing functional moieties which are reactive with active hydrogen groups and/or epoxy groups of the resin component, wherein the crosslinker component is a polyfunctional (cyclic imido)-1,3,5-triazine compound or prepolymer containing at least two cyclic imido groups as described below. Preferably, (i) and (ii) are present in a functional groups equivalents ratio of from about 0.5:1 to about 2:1.

Another aspect of the present invention relates to certain novel at least bis-imido 1,3,5-triazine compounds represented by the formula (I):

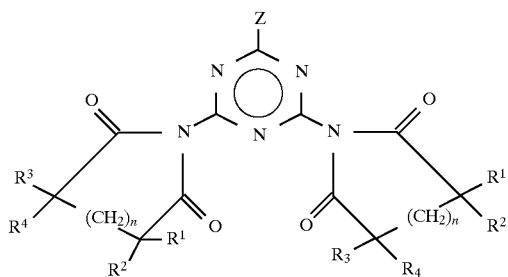
(I)

wherein Z is selected from the group consisting of hydrogen, hydrocarbyl, hydrocarbyloxy, hydrocarbylthio, amido, sulfonamido, hydrocarbylamino, cyclic amino, amino, acyl, halogen and imido represented by

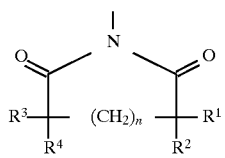

wherein $R^1$, $R^2$, $R^3$ and $R^4$ are independently selected from hydrogen, alkyl having 1 to 12 carbon atoms, alkenyl having 1 to 12 carbon atoms, alkoxy having 1 to 6 carbon atoms, aryl having 6 to 20 carbon atoms and aralkyl having 7 to 20 carbon atoms, and $R^1$ and $R^2$ can form together a methylene or $R^2$ and $R^4$ can form together an aliphatic ring having up to 6 carbon atoms which may be substituted by one or more alkyl having 1 to 12 carbon atoms, alkoxy having 1 to 6 carbon atoms, aryl having 6 to 20 carbon atoms and aralkyl having 7 to 20 carbon atoms, and n is zero or 1.

The imido groups of the at least bis-imido 1,3,5-triazine compounds agents of this invention include, without limitation, succinimido, the 2,6 diketo-piperidine group, tetrahydrophthalimido, hexahydrophthalimido and methyl-hexahydropthalimido. Preferably, the imido substitution is succinimido.

As indicated above, the invention also relates to curable compositions comprising at least bis-imido 1,3,5-triazine compound crosslinking agents and a polyfunctional active hydrogen-containing material. The at least bis-imido 1,3,5-triazine compound crosslinking agent employed in the curable composition is represented by the formula (II):

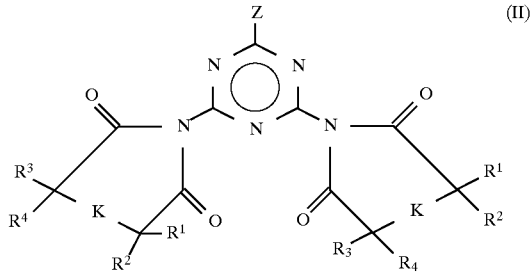
(II)

wherein Z is selected from the group consisting of hydrogen, hydrocarbyl, hydrocarbyloxy, hydrocarbylthio, amido, sulfonamido, hydrocarbylamino, cyclic amino, amino, acyl, halogen and imido represented by

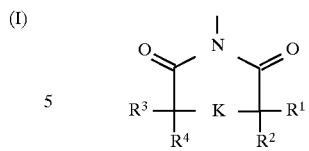

wherein $R^1$, $R^2$, $R^3$ and $R^4$ are independently selected from hydrogen, alkyl having 1 to 12 carbon atoms, alkenyl having 1 to 12 carbon atoms, alkoxy having 1 to 6 carbon atoms, aryl having 6 to 20 carbon atoms, and aralkyl having 7 to 20 carbon atoms, and $R^1$ and $R^2$ can form together a methylene or $R^2$ and $R^4$ can form together an aliphatic bridge having up to 6 carbon atoms which may be substituted by one or more alkyl having 1 to 12 carbon atoms, alkoxy having 1 to 6 carbon atoms, aryl having 6 to 20 carbon atoms and aralkyl having 7 to 20 carbon atoms, and K is selected from the group consisting of a single bond, a divalent methylene radical and a double bond, provided that K is only a double bond when $R^2$ and $R^4$ form together an aromatic ring.

Another embodiment of this invention relates to prepolymers having at least bis-imido functionality. Such prepolymers comprise the reaction product of a polyfunctional (cyclic imido)-1,3,5-triazine containing at least two cyclic imido groups, such as the at least bis-imido 1,3,5-triazine crosslinking agent represented by the formula II, and a polyfunctional active hydrogen-containing material, wherein the reaction product is substantially free of gelation. The invention is also directed to curable coating compositions containing the prepolymer and a polyfunctional resin.

At least bis-imido functional prepolymers of this invention may be represented by the formula (III):

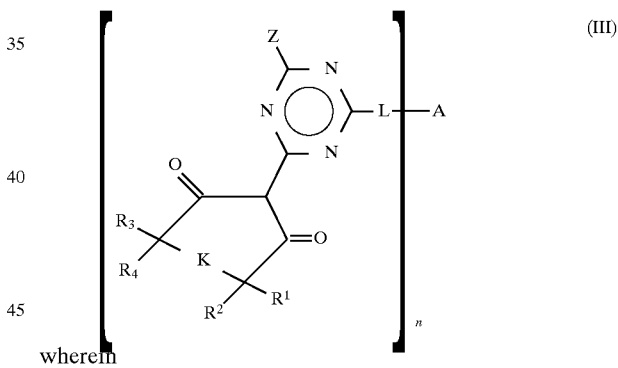
(III)

wherein
A is an n-functional anchor having n-functional nucleophilic sites,
n is at least 2,
L is a divalent bridge, and
Z is selected from the group consisting of hydrogen, hydrocarbyl, hydrocarbyloxy, hydrocarbylthio, amido, sulfonamido, hydrocarbylamino, cyclic amino, amino, acyl, halogen and imido represented by

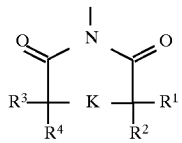

wherein $R^1$, $R^2$, $R^3$ and $R^4$ are independently selected from hydrogen, alkyl having 1 to 12 carbon atoms, alkenyl having 1 to 12 carbon atoms, alkoxy having 1 to 6 carbon atoms, aryl having 6 to 20 carbon atoms, and aralkyl having 7 to 20 carbon atoms, and $R^1$ and $R^2$ can form together a methylene or $R^2$ and $R^4$ can form together an aliphatic bridge having up to 6 carbon atoms which may be substituted by one or more alkyl having 1 to 12 carbon atoms, alkoxy having 1 to 6 carbon atoms, aryl having 6 to 20 carbon atoms and aralkyl having 7 to 20 carbon atoms, and K is selected from the group consisting of a single bond, a divalent methylene radical and a double bond, provided that K is only a double bond when $R^2$ and $R^4$ form together an aromatic ring. Preferably n is 2 to 6.

Another aspect of this invention is directed to at least bis-imido functional prepolymers represented by the formula IV:

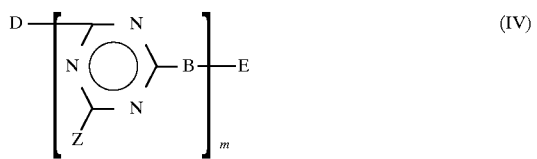
(IV)

wherein

B is a divalent group of a difunctional active hydrogen-containing material;

Z is selected from the group consisting of hydrogen, hydrocarbyl, hydrocarbyloxy, hydrocarbylthio, amido, sulfonamido, hydrocarbylamino, cyclic amino, amino, acyl, halogen and imido represented by

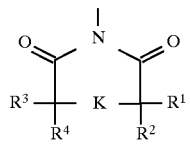

wherein $R^1$, $R^2$, $R^3$ and $R^4$ are independently selected from hydrogen, alkyl having 1 to 12 carbon atoms, alkenyl having 1 to 12 carbon atoms, alkoxy having 1 to 6 carbon atoms, aryl having 6 to 20 carbon atoms and aralkyl having 7 to 20 carbon atoms, and $R^1$ and $R^2$ can form together a methylene or $R^2$ and $R^4$ can form together an aliphatic bridge having up to 6 carbon atoms which may be substituted by one or more alkyl having 1 to 12 carbon atoms, alkoxy having 1 to 6 carbon atoms, aryl having 6 to 20 carbon atoms and aralkyl having 7 to 20 carbon atoms, and K is selected from the group consisting of a single bond, a divalent methylene radical and a double bond, provided that K is only a double bond when $R^2$ and $R^4$ form together an aromatic ring;

D is Z or HB—, wherein Z and B are as previously described; and

E is Z or an imido triazine group represented by

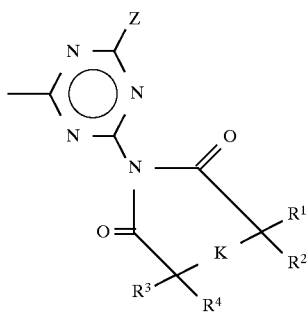

wherein Z, $R^1$, $R^2$, $R^3$, $R^4$ and K are as previously described; and m is from 0 to 100, provided that said prepolymer has at least two pendant imido groups.

Yet another embodiment of the invention is directed to a process for preparing a polyfunctional (cyclic imido)-1,3,5-triazine containing at least two cyclic imido groups, such as the at least bis-imido 1,3,5-triazine crosslinking agent represented by Formula (II), said process comprising the step of contacting cyanuric halide, such as cyanuric chloride, in the presence of an amine base with a cyclic imide such as an imide represented by the formula

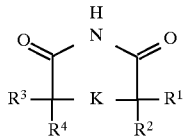

wherein $R^1$, $R^2$, $R^3$, $R^4$ and K are as previously described, to provide the at least bis-imido 1,3,5-triazine crosslinking agent.

Still yet another embodiment of the present invention is directed to a process for preparing a polyfunctional (cyclic imido)-1,3,5-triazine containing at least two cyclic imido groups, such as the bis-imido 1,3,5-triazine crosslinking agent represented by Formula II, said process comprising the step of contacting melamine with cyclic anhydride such as an anhydride represented by the formula

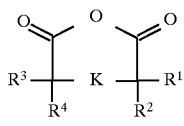

wherein $R^1$, $R^2$, $R^3$, $R^4$ and K are as previously described, to provide the bis-imido 1,3,5-triazine crosslinking agent.

Another embodiment of this invention is directed to a process for preparing an at least bis-imido functional prepolymer represented by Formula IV, said process comprising contacting (a) at least one imido functional 1,3,5-triazine represented by the formula

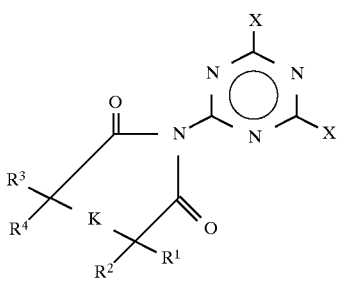

wherein X is selected from the group consisting of hydrogen, hydrocarbyl, hydrocarbyloxy, hydrocarbylthio, amido, sulfonamido, hydrocarbylamino, cyclic amino, amino, acyl, halogen and or imido represented by

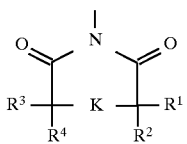

wherein $R^1$, $R^2$, $R^3$, $R^4$ and K are previously described, provided that at least one X is halogen, and (b) a difunctional active hydrogen-containing material to form the at least bis-imido functional prepolymer.

A further embodiment of the invention is directed to yet another process for preparing an at least bis-imido functional prepolymer represented by Formula IV, said process comprising the steps of: (a) contacting cyanuric halide and a difunctional active hydrogen-containing material to provide a halide functional triazine prepolymer; and (b) contacting said halide functional triazine prepolymer with an imide represented by the formula

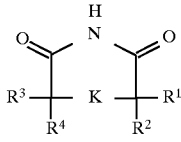

wherein $R^1$, $R^2$, $R^3$, $R^4$ and K are as previously described, to provide the at least bis-imido functional prepolymer.

These and other features and advantages of the present invention shall be more readily understood by those of ordinary skill in the art from a reading of the following detailed description.

DETAILED DESCRIPTION OF THE PREFERRED EMBODIMENTS

The at least bis-imido 1,3,5-triazine crosslinking agents of this invention are described by previously set forth Formulas (I) and (II). Without being bound to theory, it is believed that the imido functionality of the crosslinking agents of this invention undergo a ring opening to react with functional resin component during cure. Since the imido group or a part thereof is not cleaved from the triazine during the crosslinking, no volatile organic compounds (VOCs) are released. This is particularly advantageous since the release of VOCs during cure can result in deformation to the cured coating, such as in the form of pin holes and the like. The at least bis-imido 1,3,5-triazine crosslinking agents of this invention can be employed to provide solvent resistant cured coatings without the release of volatiles during cure.

The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl and alkaryl). More specifically, hydrocarbyl includes (but is not limited to) such groups as alkyl, cycloalkyl, aryl, aralkyl, alkaryl, alkenyl and cycloalkenyl, preferably having up to 24 carbon atoms. A hydrocarbyl may optionally contain a carbonyl group and/or a heteroatom (such as an oxygen, sulfur or nitrogen) in the chain or ring. A hydrocarbyl may also optionally possess pendant and/or terminal functionality such as, for example, active hydrogen containing groups such as hydroxyl, amino, carboxyl, thio, amido and activated methylene; isocyanato; cyano; epoxy; ethylenically unsaturated groups such as allyl, acryloyl and methacryloyl, and maleate and maleimido; and halo.

Preferably Z is amino, alkyl amino, methyl, phenyl, cyclohexyl or imido. Most preferably, Z is imido. It is also preferable that n is zero and that $R^1$, $R^2$, $R^3$ and $R^4$ are either hydrogen, lower alkyl having 1 to 6 carbon atoms or $R^2$ and $R^4$ form together an aliphatic bridge resulting in a six membered carbon ring which can be unsaturated or saturated. Most preferably $R^1$, $R^2$, $R^3$ and $R^4$ are hydrogen and n is zero, i.e., the imido group is succinimido.

Exemplary tris-imido 1,3,5-triazines of this invention are represented, without limitation, by the following formulae:

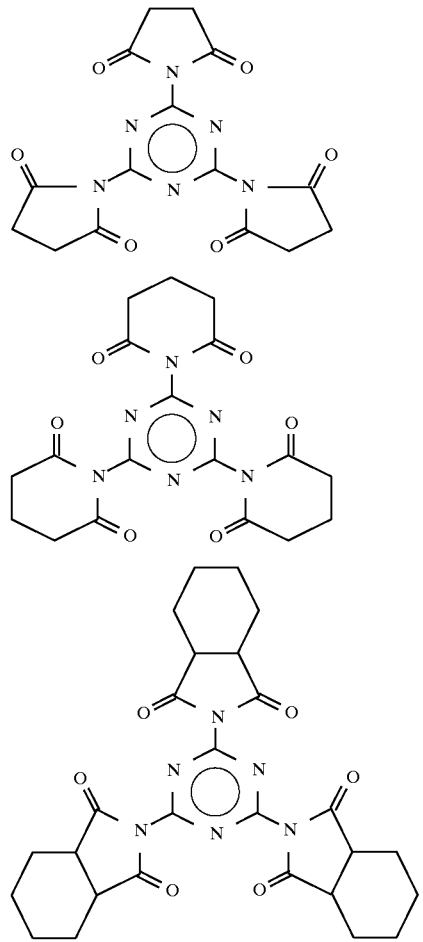

-continued

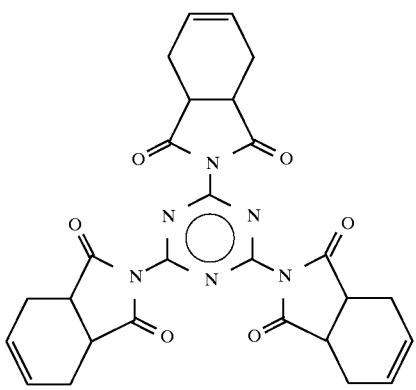

Similarly, exemplary bis-imido 1,3,5-triazines of this invention are represented, without limitation, by the following formula:

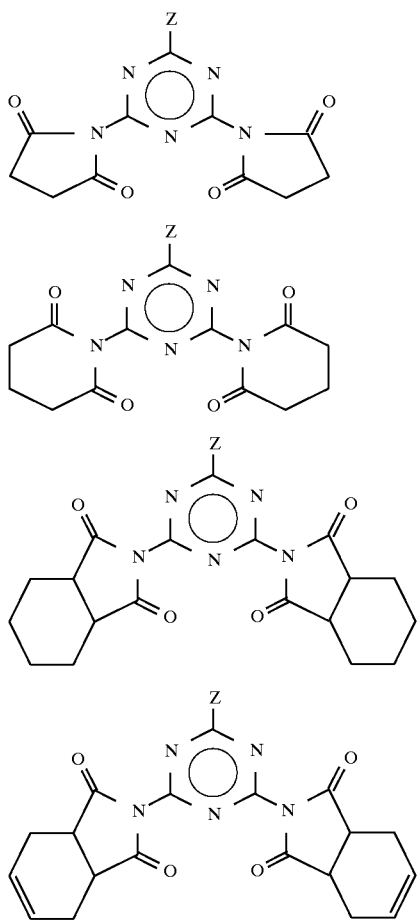

wherein Z is selected from the group consisting of hydrogen, hydrocarbyl, hydrocarbyloxy, hydrocarbylthio amido, sulfonamido, hydrocarbylamino, halogen and cyclic amino. The preferred halogens are chloro and bromo, more preferably chloro. Most preferably, Z is amino, methyl, phenyl or cyclohexyl.

The at least bis-imido 1,3,5-triazines of this invention may be prepared by the process of reacting an imide salt with cyanuric chloride such as illustrated in U.S. Pat. No. 3,794,641, the disclosure of which is incorporated by reference as if fully set forth. Cyanuric chloride is commercially available. In addition, the imide salts are either available or may be readily prepared by one of ordinary skill in the art from available imides.

This invention is also directed to a novel process for preparing at least bis-imido 1,3,5-triazines. This process comprises contacting an imide with cyanuric chloride in the presence of an amine base. It has been found that this process advantageously provides at least bis-imido 1,3,5 triazines of greater yield and purity than those produced using an imide salt. The amine bases used in the process of this invention, include without limitation, triethylamine, dimethylaminopyridine (DMAP), diisopropylethylamine and the like. Any amine base may be employed which provides the appropriate at least bis-imido 1,3,5-triazine, although triethylamine is particularly preferred for the preparation of 2,4,6-tris(succinimido)-1,3,5-triazine. The reaction products of the process of this invention may be isolated and purified by methods well known to those of ordinary skill in the art.

Another advantageous process of this invention is directed to the preparation of bis-imido 1,3,5-triazines by contacting melamine with an anhydride. This process is particularly advantageous since melamine is a relatively low cost commercially available starting material. In addition, the anhydrides are either available or can be readily prepared from available anhydrides by those skilled in the art. Exemplary anhydrides include, without limitations, succinic anhydride, phthalic anhydride, tetrahydrophthalic anhydride, hexahydrophthalic anhydride and the like.

This invention is also directed to curable compositions comprising the at least bis-imido 1,3,5-triazine crosslinking agents represented by Formula (II) and functional resin containing active hydrogen and/or epoxy moieties. Optionally and preferably, the curable composition of this invention also incudes a cure catalyst.

The polyfunctional active hydrogen-containing materials employed in this composition include those known to one skilled in the art having at least two hydrogen containing nucleophilic reactive groups. Exemplary compounds which have at least two reactive groups can be selected from the group consisting of carboxyl, hydroxy, thiol, sulfonamide, amido, primary amine, secondary amine (including imine), salts thereof and mixtures thereof. The active hydrogen-containing materials useful herein are typically film-forming compositions, which form crosslinked network in the resultant cured compositions. Illustrative examples of active hydrogen-containing materials are shown in U.S. Pat. No. 4,435,559, the disclosure of which is incorporated by reference herein. Typical of such materials are polyurethanes, acrylic polymers, polyesters, epoxy resins such as —OH and —NH containing epoxy prepolymers, alkylene polyamines, such as hexamethylene diamine, and the like.

Especially suitable polyfunctional active hydrogen containing materials include polyesters and polyacrylates containing pendant hydroxyl groups as reaction sites. The former are obtained in a known manner by, for example, the reaction of polycarboxylic acids with excess quantifies of polyhydric alcohols; the latter are obtained by the copolymerization of acrylic or methacrylic acid derivatives with hydroxyl-group-containing derivatives of these acids, such as, for example, the hydroxyalkyl esters, optionally with the simultaneous use of additional vinyl compounds, such as, for example, styrene. Hydroxyl-group-containing polyurethanes can be obtained in a known manner by the reaction of polyisocyanates with excess quantities of compounds containing at least two hydroxy groups. Suitable commercially available hydroxy-group-containing polyesters are CYPLEX® 1531, available from CYTEC Industries, Cargil Polyester 3000, 3016, 3018, 3020 and 5776, available from Cargil. Suitable hydroxy functional acrylic resins are available commercially from S. C. Johnson & Son, Inc. under the trademark JONCRYL®-500, a copolymer of 50% styrene, 20% hydroxypropyl methacrylate and 30% butyl acrylate, and from Rohm & Haas Co. under the trademark AT-500. Also suitable for use are hydroxy-terminated polycaprolactones, such as TONE 0200 available from Union Carbide Corp.

The curable composition optionally also includes a cure catalyst. Such cure catalysts are well known to those skilled in the art and include, for example, methyl toluene sulfonimide (MTSI) and para-toluene sulfonic acid (P-TSA). Other typical cure catalysts include a metal salt and/or a compound or a complex of a metal such as lead, zinc, iron, tin, titanium and manganese, preferably tin. Suitable salts of these metals are, for example acetates, octoates, laurates and naphthenates. Suitable organometallic compounds, for example, are tetrabutyldiacetoxy stannoxane, dibutyltin dilaurate, dimethyltin dilaurate or an acetyl acetonate.

Quaternary and ternary compounds may also be utilized as catalysts. Generally, the ternary or quaternary catalysts are known compounds of the formulas:

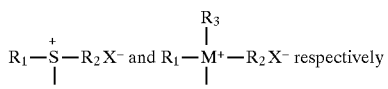

wherein $R_1$, $R_2$, $R_3$ and $R_4$ may be equivalent or different and may be $C_1$ to $C_{20}$ aliphatic, aromatic, benzylic, cyclic aliphatic and the like, where M may be nitrogen, phosphorous or arsenic (to provide, respectively, quaternary ammonium, phosphonium or arsonium compounds), where S is sulfur (to provide a ternary sulfonium compound), and where $X^-$ may be hydroxide, alkoxide, bicarbonate, carbonate, formate, acetate lactate, and other carboxylates derived from volatile organic carboxylic acids or the like.

When employed, the cure catalyst is used in the curable compositions of this invention in amounts effective to accelerate cure at the temperature employed. For example, the catalyst is typically used in amounts of from about 0.01 to about 2.0% by weight based on the weight of the curable compositions.

In the practice of the invention, the curable compositions can be adapted for use in solvent-based, water-based, and powder coating compositions depending on the properties, e.g., liquid or solid, of the particular composition. Coating compositions comprising aqueous dispersions are particularly suited to application by electrodeposition. Typically, the compositions will contain about 1 to 100 percent, by weight, of combined polyfunctional resin and crosslinker, and the weight ratio crosslinker:resin will range from about 5:95 to about 50:50. Preferably, depending on the relative equivalent weights of the crosslinker and resin, the weight ratios would be from about 15 to 40 parts crosslinker to about 60 to 85 parts resin.

The at least bis-imido 1,3,5-triazine crosslinking agents of this invention can be advantageously employed in curable powder coating compositions. A particularly preferred crosslinking agent for use in powder coatings is 2,4,6-tris (succinimido)-1,3,5-triazine.

In many instances, a pigment composition and various other conventional additives such as antioxidants, surface active agents, coupling agents, flow control additives, and the like, can be included in the curable composition of this invention. The pigment composition may be of any conventional type, such as iron oxides, lead oxides, strontium chromate, carbon black, titanium dioxide, talc, barium sulfate, cadmium yellow, cadmium red, chromic yellow, or the like.

For example, a typical curable powder coating composition may contain about 20 weight percent of a pigment such as titanium oxide (e.g., R-960 available from E. I. du Pont de Nemours & Co.) and about 0.5 to about 1.0 weight percent of catalyst, if desired or necessary, based on the combined weight of crosslinker and polyfunctional active hydrogen-containing backbone. In addition, a typical composition may also contain flow control additives, such as RESIFLOW® P 67 (an acrylic polymer absorbed on silica available from Estron Corp.) and benzoin, each in an amount of about 1 weight percent based on the total weight of the crosslinker, backbone, and titanium oxide pigment. The weight ratio of the crosslinking agent and the resin in the powder coating composition will depend on the equivalent weights of these two components and can be readily ascertained by one of ordinary skill. The amount of crosslinking agent employed is typically in the range from about 3 to about 30 weight percent, and preferably in the range of from about 6 to about 25 weight percent based on the combined weight of the crosslinking agent and resin. Conversely, the amount of resin is typically in the range of from about 70 to about 97 weight percent, and preferably in the range of about 75 to about 95 weight percent of their combined weight.

The powder coating composition of the present invention can be used by depositing the powder coating composition on a substrate by any well-known means such as a powder gun, electrostatic depositions or deposition from a fluidized bed. After application to a substrate, such as a steel panel, the powder coating composition is heated to a temperature sufficient to cause the particles to flow and cure by any conventional method, such as in baking ovens or with banks of infrared heat lamps or any other means available to those skilled in the art. Depending on the particular selection of components, the powder is heated to temperatures between about 110° C. and about 230° C., preferably between about 150° C. and about 230° C., and more preferably about 170° C. to about 200° C.

This invention also includes prepolymers of at least bis-imido 1,3,5-triazine compounds and polyfunctional active hydrogen-containing material. These prepolymers can be particularly advantageous for preparing homogeneous curable powder coating compositions. For example, the homogeneity of a curable powder coating composition containing 2,4,6-tris(succinimido)-1,3,5-triazine may be improved by using a prepolymer of the succinimido triazine.

These prepolymers may be prepared by reacting at least bis-imido 1,3,5-triazine compounds with a polyfunctional active hydrogen-containing material. The reaction product is substantially free of gelation. Gelation occurs when a curable composition reaches its gel time as measured according to DIN Standard 55990 and as disclosed in Tosko Aleksandar Misev, Powder Coatings: Chemistry and Technology, John Wiley & Sons, Inc. 288–89 (1991).

The reaction temperature used to prepare these prepolymers can be varied so long as the prepolymer is substantially free of gelation. Generally, such prepolymers are prepared at a reaction temperature in the range of from about 125° C. to about 150° C. for a time period that does not result in gelation.

These prepolymers can be prepared from the same or different polyfunctional active hydrogen-containing material used in the curable compositions of this invention. Thus, a prepolymer can be prepared by partially reacting a mixture of an at least bis-imido 1,3,5-triazine and a polyfunctional active hydrogen-containing material to form a curable composition containing an at least bis-imido functional prepolymer and the unreacted polyfunctional active hydrogen-containing material. If necessary or desired additional polyfunctional active hydrogen-containing material, which can be the same or different from the partially reacted active hydrogen-containing material, may be added to the composition. This curable composition may then be applied to a substrate and cured.

Alternatively, such prepolymers can be prepared by fully reacting an amount of polyfunctional active hydrogen-containing material and an at least bis-imido 1,3,5-triazine, wherein both components are present in an amount effective to provide a prepolymer having at least bis-imido functionality. Preferably, the polyfunctional active hydrogen-containing material for forming a prepolymer having at least bis-imido functionality is selected from the group consisting of trimethylolpropane (TMP), pentaerythritol, ethylene glycol, hexanediol, butanediol, diamines and triamines. The hydroxy functional materials are preferred, more preferred are low equivalent weight hydroxy functional material and most preferred is TMP. A prepolymer prepared in this manner may then be combined with the same or different polyfunctional active hydrogen material to provide a curable composition which can then be applied to a substrate and cured as desired.

The prepolymers represented by formula (III) have an n-functional anchor A having n-functional nucleophilic sites. The n-functional nucleophilic sites can be the same or different and are derived from reactive groups selected from the group consisting of carboxyl groups, hydroxy groups, thiol groups, sulfonamide groups, carbamate groups, amido groups, primary amine groups, secondary amine groups, salts thereof and mixtures thereof. The polyfunctional active hydrogen-containing materials described herein may be used to form the n-functional anchor A.

The reactive groups of the polyfunctional active hydrogen containing materials act as nucleophiles which cause a ring opening of the imido groups of the at least bis-imido 1,3,5-triazine at the nitrogen-carbonyl bond of the imido group. This ring opening results in the formation of a divalent bridge L which covalently bonds the triazine ring and the nucleophilic site of the n-functional anchor A. The divalent bridge L can be represented by the formula

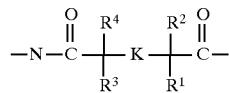

wherein $R^1$, $R^2$, $R^3$, $R^4$ and K are as previously described.

For example, if a prepolymer is formed using trimethylolpropane as the polyfunctional active hydrogen-containing material to form the n-functional anchor A, then the bridge L between the triazine and the n-functional anchor A can be illustrated as follows:

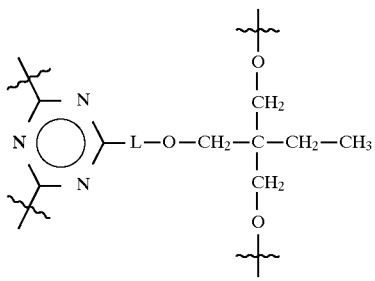

or more specifically as

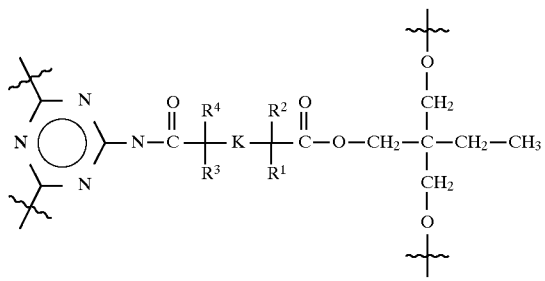

wherein L, K, $R^1$, $R^2$, $R^3$ and $R^4$ are as previously described.

Yet another prepolymer of the present invention is represented by previously described formula (IV). These prepolymers, which are the reaction product of halogenated triazines and difunctional active hydrogen-containing material, have at least two pendant imido groups.

The at least bis-imido functional prepolymers described by formula (IV) contain a divalent group B derived from a difunctional active hydrogen-containing material. The two reactive groups of such difunctional materials can be the same or different and may be selected from the group consisting of carboxyl groups, hydroxy groups, theol groups, sulfonamide groups, amido groups, primary amine groups, secondary amine groups, salts thereof and mixtures thereof. Preferably, the difunctional active hydrogen-containing material is selected from diols or diamines, such as, for example, neopentyl glycol or 1,6-hexamethylene diamine, respectively. Generally, the difunctional active hydrogen-containing material forms the divalent group B by attack at the halogenated position of two triazines resulting in the formation of two covalent bonds linking the difunctional material and the two triazines after the elimination of the active hydrogen and halogen atom at each bonding site.

These prepolymers of formula (IV) may be used to prepare curable compositions in the manner previously described for the at least bis-imido 1,3,5-triazine crosslinking agents of this invention by combination with a functional resin component and optionally a cure catalyst.

This invention also includes two novel processes for preparing the prepolymers represented by formula (IV). One novel process comprises reacting at least one imido functional 1,3,5-triazine having at least mono-halo functionality with a difunctional active hydrogen-containing material. The molar ratio and degree of halide functionality may be varied to control the size and structure of the resulting prepolymers. Such manipulation is well known to one of ordinary skill in the art and can be readily achieved without undue experimentation.

For example, a 2,4-bis(imido)-6-halo-1,3,5-triazine may be reacted with a difunctional active hydrogen-containing material at a molar ratio of 2:1 to obtain a prepolymer having four imido groups pendant to two triazine rings linked by the difunctional active hydrogen containing material. Such a prepolymer may be represented, for example, by the formula (V):

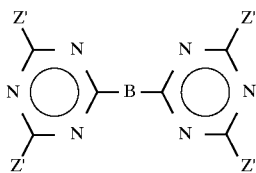

wherein Z' is imido and B is a divalent group derived from the difunctional active hydrogen-containing material.

Alternatively, the above described reaction mixture can be altered by including a molar equivalent amount of a bis-halo functional triazine and the difunctional active hydrogen-containing material along with a lesser amount of the mono-halo functional triazine. This reaction mixture results in the formation of prepolymers having repeating units derived from the bis-halo functional triazine and difunctional material with the terminal ends of the prepolymer derived from the mono-halo functional triazine. Such a prepolymer may be represented, for example, by the formula (VI):

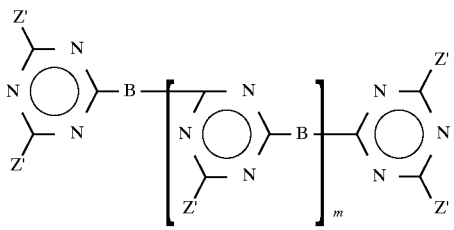

wherein Z' is imido, B is a divalent group derived from the difunctional active hydrogen-containing material and m is 0 to 100. The components and molar ratios thereof can be readily altered by one of ordinary skill in the art to obtain the described prepolymers employing this novel process. For example, an excess of the difunctional active hydrogen-containing material could be employed to obtain a prepolymer having terminal ends derived from the difunctional active hydrogen containing material and thus having active hydrogen functionality.

Preferably, the halo functional triazines employed in this process are chloro functional. It is also preferable to conduct the above-described reaction under an inert atmosphere, such as a nitrogen atmosphere. The reaction may be conducted at ambient temperature or any other temperature which promotes the desired prepolymeric product.

The second novel process for preparing prepolymers described by formula (IV) comprises first reacting cyanuric halide with a difunctional active-hydrogen containing material and subsequently reacting the product thereof with an imide. Preferably the cyanuric halide is cyanuric chloride. This process typically provides the prepolymer of formula (IV) as well as oligomers of those prepolymers. This reaction is preferably conducted at room temperature under an inert atmosphere, such as nitrogen.

The examples which follow are intended as an illustration of certain preferred embodiments of the invention, and no limitation of the invention is implied.

EXAMPLE 1

Preparation of 2,4,6-Tris (succinimido)-1,3,5-triazine from the Potassium Salt of Succinimide and Cyanuric Chloride A solution of potassium hydroxide (29 g) in 150 mL of ethanol was added to a hot solution of succinimide (50 g) in 100 mL of ethanol. The solution was then cooled in an ice bath and the potassium salt of succinimide was precipitated and filtered (60 g). To a mixture of the potassium salt (60 g) in 200 mL of t-butanol at 0° C. was slowly added cyanuric chloride. The mixture was warmed up to ambient temperature and stirred overnight. Then the mixture was heated to 60° C. for 2 hours. The t-Butanol was evaporated under vacuum to give brown solids, which were washed with a dilute HCl solution and methanol (45 g). Solids (15 g) with light yellow color were obtained after washing with hot dimethylformamide, mp >300° C. C-13 NMR (DMSO-$d_6$) showed 3 peaks at 176 ppm, 166 ppm and 30 ppm, and proton NMR showed a singlet at 2.93 ppm. The molecular ion of the title compound was observed by mass spectroscopy.

EXAMPLE 2

Preparation of 2,4-Bis (succinimido)-6-amino-1,3,5-triazine from Melamine and Succinic Anhydride Melamine was treated with 9 moles of succinic anhydride at 150° C. without solvent for 2 hours. The mixture was washed with methanol, water, and acetone to give solids, 89% of the title compound with mp >300° C. $^1$H-NMR (DMSO-$d_6$) showed 2 singlets at 8.65 ppm and 2.90 ppm with an 1:4 ratio. C-13 NMR showed 4 peaks at 175 ppm, 169 ppm, 162 ppm and 29 ppm.

EXAMPLE 3

Powder Coating Formulation

A curable powder coating composition having the following components was prepared:

| Components | Amount grams |
|---|---|
| Benzoin | 0.30 |
| R960 Rutile TiO$_2$ DuPont | 6.70 |
| Resiflow ® P-67 flow control additive | 0.30 |
| RUCOTE ® 104 | 12.50 |
| TBDAS | 0.33 |
| TSST | 4.20 |
| (Prepared according to Ex. 1) | |

TBDAS — tetrabutyldiacetoxy stannoxane
TSST — 2,4,6-tris(succinimido)-1,3,5-triazine
RUCOTE ® 104 — polyhydroxy functional polyester available from Ruco Polymer Corp, Hicksville, New York The curable powder composition was applied to BO-1000 (iron phosphate treated steel panels) substrates and cured. The cure parameters and film properties of the cured coatings are set forth below in Table 1.

TABLE 1

| Substrate | BO1000 | BO1000 |
|---|---|---|
| Bake Temp (°C.) | 175 | 190 |
| Bake Time (Min) | 20 | 20 |
| MEK RUBS | +200 | +200 |
| Film Thickness (mils) | 1.8/2.1 | 1.7/1.9 |
| KHN (Knoop Hardness at 25° C.) | 16.4 | 14.3 |
| Pencil Hardness | 3H–4H | H–2H |
| Impact F/R (In. lbs) | 40/10 | 50/20 |
| Gloss 60 (deg.) | 50.0 | 52.0 |
| 20 (deg.) | 12.6 | 13.2 |
| Gel Time (sec.) | 277 | 277 |
| Vertical Plate Flow (CM) | 2.1 | 2.1 |
| Temp (C.)/Time (Min) | 190/20 | 190/20 |

The cured coatings had a film appearance that exhibited tight orange peel with some shallow surface depression.

EXAMPLE 4

Preparation of a Mixture of Mono- and Bis (hexahydrophthalimido)-1,3,5-triazine Melamine (1.26 g, 1 mmol) and hexahydrophthalic anhydride (22.5 g, 15 mmol) were mixed, and heated to 150° C. for 8 hours. Methylene chloride was added to wash the solids, followed by washing with water. The solids were a mixture of the bis 2,4-(hexahydrophthalimido)-6-amino-1, 3,5-triazine and hexahydrophthalic acid. NMR spectrum of the bis adduct showed a triplet of the methines at 3.19 ppm and a signal of NH at 8.60 ppm. The ratio of these two signals was 2:1.

The reaction also yielded the mono adduct of the anhydride with melamine. The mono derivative had a triplet signal at 3.08 ppm due to the methines and broad signals at 7.18 ppm due to NH. The ratio of the triplet to the NH signal was 1:2.

EXAMPLE 5

Preparation of 2,4,6-tris(succinimido)-1,3,5-triazine from Cyanuric Chloride and Succinimide with Triethylamine Succinimide (59.4 g; 0.6 moles) and methylene chloride (300 ml) were placed in a 1000 ml flask equipped with a mechanical stirrer, nitrogen inlet, condenser and addition funnel. The mixture was stirred to partially dissolve the imide. Triethylamine (6.10 g; 0.6 moles) was then added to the slurry and stirred for 0.5 hour. Cyanuric chloride (36.9 g; 0.2 moles) was dissolved in acetone (175 ml) and the mixture was added dropwise by the addition funnel to the imide slurry over a 75 minute period. After addition of all the cyanuric chloride the slurry had an off-white color and was stirred at room temperature overnight. The solids were filtered and washed with methylene chloride (2×200 ml). Next the dried solids were suspended in water (200 ml), stirred, filtered and washed further with water. The wet solids were placed in acetone (200 ml), stirred, filtered and further washed with acetone followed by drying. Yield=48.9 g (~66%).

EXAMPLE 6

Preparation of 2,4-bis(hexahydrophthalimido)-6-diethylamino-1,3,5-triazine

Hexahydrophthalimide (500 mg; 3.27 mmol), methylene chloride (10 ml) and triethylamine (330 mg; 3.27 mmol) were stirred under a nitrogen atmosphere. To the stirred solution was added dropwise a solution of cyanuric chloride (151 mg; 0.82 mmol) in acetone (5 ml) over a 10 minute period. After 5 to 10 minutes a solid precipitated to form a slurry that was stirred overnight. The solids were then filtered and the organic filtrate was diluted with methylene chloride and washed twice with water in a sepratory funnel. The organic phase was dried over $Na_2SO_4$ and concentrated in vacuo to give a solid. The major product of the solid was the title compound.

EXAMPLE 7

Preparation of 2,4,6-tris (hexahydrophthalimido)-1,3,5-triazine

A mixture of hexahydrophthalimide (1.0 g; 6.54 mmol), methylene chloride (10 ml) and N,N-dimethylaminopyridine (DMAP) (0.8 g; 6.56 mmol) was stirred under nitrogen at room temperature for 0.5 hours. A solution of acetone (5 ml) and cyanuric chloride (0.4 g; 2.17 mmol) was added dropwise to the mixture over a 1 hour period. A thick slurry was formed and stirred overnight. The reaction mixture was then diluted with methylene chloride, followed by the addition of water to dissolve the solids. The biphasic mixture was washed with water in a sepratory funnel. The organic layer was separated, dried over $Na_2SO_4$ and concentrated under reduced pressure. A pale yellow semi-solid was obtained. The solid was subjected to thin layer chromatography (ethyl acetate eluent) and the title compound was separated and identified by $^{13}C$ NMR.

EXAMPLE 8

Powder Coating Composition

A curable powder coating composition was prepared in a manner substantially similar to Example 3, except the 2,4,6-tris(succinimido)-1,3,5-triazine prepared in Example 5 was employed. This curable powder coating composition was applied to BO-1000 (ion phosphate treated steel panels) substrates and cured. The cure parameters and film properties of the cured coating are set forth below in Table 2.

TABLE 2

| Substrate | BOO1000 | BO1000 | BO1000 |
|---|---|---|---|
| Bake Temp (°C.) | 175 | 190 | 200 |
| Bake Time (Min) | 20 | 20 | 20 |
| MEK RUBS (mar/rmv) | 10/175 | 50/200+ | 75/200+ |
| Film Thickness (mils) | 1.5–1.9 | 1.7–2.0 | 1.5–2.0 |
| KHN (Knoop Hardness at 25° C.) | ~15* | ~15* | — |
| Pencil Hardness | 2H | 2H–3H | 2H–3H |
| Impact | <10 | <10 | <10 |
| Gloss 60 (deg.) | 58 | 58 | 60 |
| 20 (deg.) | 15 | 15 | 15 |

*Unable to obtain a symmetrical diamond imprint

The cured coatings had a film appearance that exhibited a micro-orange peel.

EXAMPLE 9

Three moles of 2,4,6-tris(succinimido)-1,3,5-triazine and one mole of trimethylol propane (TMP) are mixed together by melting the TMP at approximately 125° C. and adding the succinimide. Then tetrabutyldiacetoxy stannoxane (TBDAS) (approximately 1 to 5% based on the combined crosslinker and active hydrogen-containing material) is added and the mixture is heated to about 160° C. with mixing to from the hexakis(succinimido) functional prepolymer.

EXAMPLE 10

Prepolymer Reaction Product of 2,4-bis (succinimido)-6-chloro-1, 3,5-triazine and Neopentyl Glycol Succinimide (1.98 g; 0.02 mole) and tetrahydrofuran (15 ml) were placed in a suitable flask under nitrogen atmosphere and stirred. Triethylamine (2.02 g; 0.02 mole) was added to the mixture and stirred for about 15 minutes. This was followed by the dropwise addition of a solution of cyanuric chloride (1.85 g; 0.10 mole) in tetrahydrofuran (6 ml) which resulted in an orange precipitate. After 4 hours, neopentyl glycol (0.54 g; 0.02 mole) and triethylamine (1.01 g; 0.01 mole) were added to the mixture and stirred overnight. Then the reaction slurry was diluted with methylene chloride and washed with water. The organic layer was separated, dried over Na$_2$SO$_4$ and concentrated in vacuo to give a brown colored oil of a prepolymer of 2,4-bis(succimido)-6-chloro-1,3,5-triazine and neopentyl glycol.

EXAMPLE 11

Prepolymer Reaction Product of 2,4-bis(phthalimido)-6-chloro-1,3,5-triazine and 1,6-hexamethylene Diamine 2,4-bis(phthalimido)-6-chloro-1,3,5-triazine (2.03 g; 0.005 mole) and acetone (10 ml) were placed in a suitable flask under a nitrogen atmosphere and stirred. Solid 1,6-hexamethylene diamine (0.29 g; 0.0025 mole) was added to the stirred slurry and stirring was continued. Next, triethylamine (0.51 g; 0.005 mole) was added and the mixture was stirred overnight. The slurry was concentrated in vacuo. The residue was placed in a mixture of water and methylene chloride, filtered and the organic layer was separated and dried oven Na$_2$SO$_4$. Solvent was removed under reduced pressure to give solids (0.8 g). $^{13}$C NMR showed the appropriate signals of a prepolymer of 2,4-bis(phthalimido)-6-chloro-1,3,5-triazine and 1,6-hexamethylene diamine.

EXAMPLE 12

Prepolymer Reaction Product of Cyanuric Chloride, 1-6-hexamethylene Diamine and Succinimide Cyanuric chloride (1.85 g; 0.01 mole), acetone (15 ml) and K$_2$CO$_3$ (0.69 g; 0.005 mole) were placed in a suitable flask under a nitrogen atmosphere. The slurry was stirred at room temperature while a solution of 1,6-hexamethylene diamine (0.58 g; 0.005 mole) in acetone (7 ml) was added dropwise over a 10 minute period. Next, succinimide (2.0 g; 0.02 mole) followed by triethylamine (2.02 g; 0.02 mole) were added to the reaction slurry and the slurry was stirred overnight. The slurry was concentrated in vacuo to give a solid residue. The solids were washed with water, filtered, washed with acetone and air dried to give a yellowish gray solid.

Other variations and modifications of this invention will be obvious to those skilled in this art. This invention is not limited except as set forth in the following claims.

What is claimed is:

1. A prepolymer represented by the formula (III):

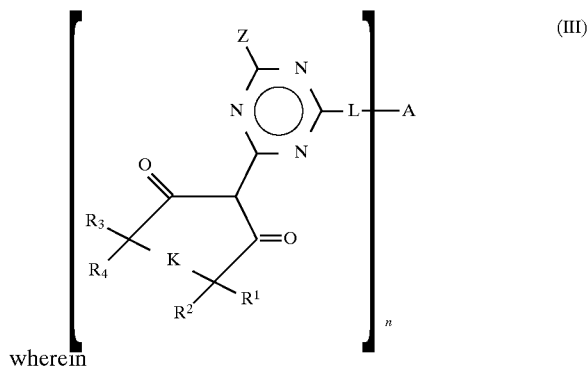

wherein

A is an n-functional anchor having n-functional nucleophilic sites, n is at least 2, L is a divalent bridge, and Z is selected from the group consisting of hydrogen, hydrocarbyl, hydrocarbyloxy, hydrocarbylthio, amido, sulfonamido, hydrocarbylamino, cyclic amino, amino, acyl, halogen and imido represented by

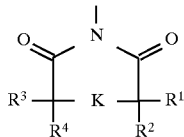

wherein R$^1$, R$^2$, R$^3$ and R$^4$ are independently selected from hydrogen, alkyl having 1 to 12 carbon atoms, alkenyl having 1 to 12 carbon atoms, alkoxy having 1 to 6 carbon atoms, aryl having 6 to 20 carbon atoms or aralkyl having 7 to 20 carbon atoms, and R$^1$ and R$^2$ can form together a methylene or R$^2$ and R$^4$ can form together an aliphatic bridge having up to 6 carbon atoms which may be substituted by one or more alkyl having 1 to 12 carbon atoms, alkoxy having 1 to 6 carbon atoms, aryl having 6 to 20 carbon atoms or aralkyl having 7 to 20 carbon atoms, and K is selected from the group consisting of a single bond, a divalent methylene radical and a double bond, provided that K is only a double bond when R$^2$ and R$^4$ form together an aromatic ring.

2. The prepolymer according to claim 1, wherein said n-functional nucleophilic sites can be the same or different and are derived from reactive groups selected from the group consisting of carboxyl groups, hydroxy groups, thiol groups, sulfonamide groups, carbamate groups, amido groups, primary amine groups, secondary amine groups, salts thereof and mixtures thereof.

3. The prepolymer according to claim 2, wherein n is 2 to 6.

4. The prepolymer according to claim 3, wherein L is represented by the formula

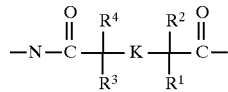

wherein R$^1$, R$^2$, R$^3$, R$^4$ and K are as previously described.

5. The prepolymer according to claim 4, wherein Z is selected from the group consisting of hydrogen, hydrocablyoxy, imido, amino, alkyl amino, methyl, phenyl, cyclohexyl and halogen.

6. The prepolymer according to claim 5, wherein the n-functional anchor is a group derived from a compound selected from the group consisting of trimethyolpropane, pentaerythritol, ethylene glycol, hexanediol, butanediol, diamines and triamines.

7. The prepolymer according to claim 5, wherein K is a single bond and R$^1$, R$^2$, R$^3$ and R$^4$ are independently selected from the group consisting of hydrogen and lower alkyl having 1 to 6 carbon atoms.

8. The prepolymer according to claim 7, wherein the n-functional anchor is a group derived from trimethyolpropane.

9. A curable coating composition comprising (a) the prepolymer of claim 1, and (b) a resin component comprising a polyfunctional resin containing functional moieties selected from active hydrogen groups or epoxy groups.

10. The curable coating composition according to claim 9, wherein the polyfunctional resin contains at least two reactive groups selected from the group consisting of carboxyl groups, hydroxy groups, thiol groups, sulfonamide groups, amido groups, primary amine groups, secondary amine groups, salts thereof and mixtures thereof.

11. The curable coating composition according to claim 10, wherein the polyfunctional resin is hydroxy-functional and is selected from the group consisting of acrylic resins, polyester resins, polyurethanes, polyols, polyether polyols, polyether sulfones and alkyds.

12. The curable coating composition according to claim 9, further comprising an effective amount of a cure catalyst to assist in curing the curable composition.

13. The curable coating composition according to claim 12, wherein the cure catalyst is a metal salt or a compound comprising tin.

14. The curable coating composition according to claim 13, wherein the cure catalyst is selected from the group consisting of tetrabutyldiacetoxy stannoxane, dibutyltin dilaurate and dimethyltin dilaurate.

15. The curable coating composition according to claim 9, wherein said composition is a powder coating composition.

16. A prepolymer having at least bis-imido functionality comprising the reaction product of:

(a) an at least bis-imido 1,3,5-triazine crosslinking agent represented by the formula (II)

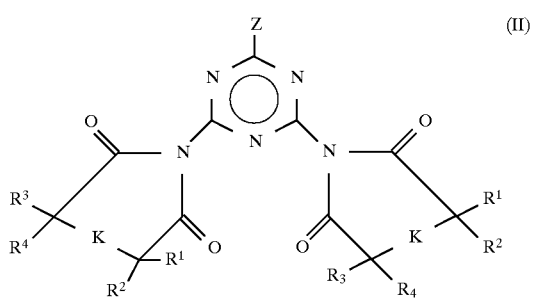
(II)

wherein Z is selected from the group consisting of hydrogen, hydrocarbyl, hydrocarbyloxy, hydrocarbylthio, amido, sulfonamido, hydrocarbylamino, cyclic amino, amino, acyl, halogen and imido represented by

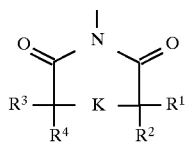

wherein $R^1$, $R^2$, $R^3$ and $R^4$ are independently selected from hydrogen, alkyl having 1 to 12 carbon atoms, alkenyl having 1 to 12 carbon atoms alkoxy having 1 to 6 carbon atoms, aryl having 6 to 20 carbon atoms, or aralkyl having 7 to 20 carbon atoms, $R^1$ and $R^2$ can form together a methylene and $R^2$ and $R^4$ can form together an aliphatic bridge having up to 6 carbon atoms which may be substituted by one or more alkyl having 1 to 12 carbon atoms, alkoxy having 1 to 6 carbon atoms, aryl having 6 to 20 carbon atoms or aralkyl having 7 to 20 carbon atoms, and K is selected from the group consisting of a single bond, a divalent methylene radical and a double bond, provided that K is only a double bond when $R^2$ and $R^4$ form together an aromatic ring; and (b) a polyfunctional active hydrogen-containing material, wherein said prepolymer is free of gelation.

17. The prepolymer according to claim 16, wherein Z is selected from the group consisting of hydrogen, hydrocarbyloxy, imido, amino, alkyl amino, methyl, phenyl, cyclohexyl and halogen.

18. The prepolymer according to claim 17, wherein the polyfunctional active hydrogen-containing material contains at least two reactive groups which can be the same or different selected from the group consisting of carboxyl groups, hydroxy groups, thiol groups, sulfonamide groups, amido groups, primary amine groups, secondary amine groups, salts thereof and mixtures thereof.

19. The prepolymer according to claim 18, wherein the polyfunctional active hydrogen-containing material is hydroxy functional and is selected from the group consisting of acrylic resins, polyester resins, polyurethanes, polyols, polyether polyols, polyether sulfones and alkyds.

20. The prepolymer according to claim 19, wherein K is a single bond and $R^1$, $R^2$, $R^3$ and $R^4$ are independently selected from the group consisting of hydrogen and lower alkyl having 1 to 6 carbon atoms.

21. The prepolymer according to claim 20, wherein Z is imido.

22. A curable coating composition comprising (a) the prepolymer according to claim 16 and (b) an unreacted resin component comprising a polyfunctional resin containing functional moieties selected from active hydrogen groups or epoxy groups.

23. The curable coating composition according to claim 22, wherein said unreacted polyfunctional resin is the same as the polyfunctional active hydrogen-containing material reacted to form the prepolymer.

24. The curable coating composition according to claim 22, wherein said unreacted polyfunctional resin is different than the polyfunctional active hydrogen-containing material reacted to form the prepolymer.

25. The curable coating composition according to claim 22, wherein said composition is a powder coating composition.

26. A prepolymer represented by the formula (IV):

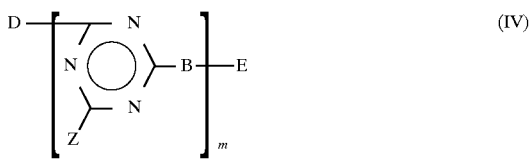
(IV)

wherein
B is a divalent group of a difunctional active hydrogen-containing material;
Z is selected from the group consisting of hydrogen, hydrocarbyl, hydrocarbyloxy, hydrocarbylthio, amido, sulfonamido, hydrocarbylamino, cyclic amino, amino, acyl, halogen and imido represented by

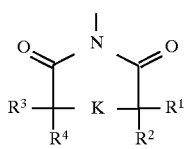

wherein $R^1$, $R^2$, $R^3$ and $R^4$ are independently selected from hydrogen, alkyl having 1 to 12 carbon atoms, alkenyl having 1 to 12 carbon atoms, alkoxy having 1 to 6 carbon atoms, aryl having 6 to 20 carbon atoms or aralkyl having 7 to 20 carbon atoms, and $R^1$ and $R^2$ can form together a methylene or $R^2$ and $R^4$ can form together an aliphatic bridge having up to 6 carbon atoms which may be substituted by one or more alkyl having 1 to 12 carbon atoms, alkoxy having 1 to 6 carbon atoms, aryl having 6 to 20 carbon atoms or aralkyl having 7 to 20 carbon atoms, and K is selected from the group consisting of a single bond, a divalent methylene radical and a double bond, provided that K is only a double bond when $R^2$ and $R^4$ form together an aromatic ring;

D is Z or HB—, wherein Z and B are as previously described; and

E is Z or an imido triazine group represented by

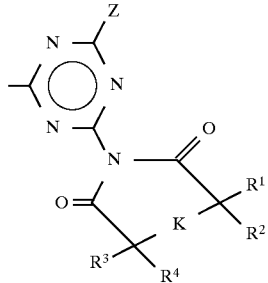

wherein

Z, $R^1$, $R^2$ $R^3$, $R^4$ and K are as previously described; and m is from 0 to 100, provided that said prepolymer has at least two pendant imido groups.

27. The prepolymer according to claim 26, wherein the difunctional active hydrogen-containing material comprises two reactive groups which can be the same or different selected from the group consisting of carboxyl groups, hydroxy groups, thiol groups, sulfonamide groups, amido groups, primary amine groups, secondary amine groups, salts thereof and mixtures thereof.

28. The prepolymer according to claim 27, wherein D is imido and E is the imido triazine group.

29. The prepolymer according to claim 28, wherein Z is imido.

30. The prepolymer according to claim 29, wherein the difunctional active hydrogen-containing material is selected from the group consisting of diols and diamines.

31. The prepolymer according to claim 30, wherein m is 0 to 20.

32. The prepolymer according to claim 31, wherein K is a single bond and $R^1$, $R^2$, $R^3$ and $R^4$ are independently selected from the group consisting of hydrogen and lower alkyl having 1 to 6 carbon atoms.

33. A curable composition comprising (a) the prepolymer according to claim 26, and (b) a resin component comprising a polyfunctional resin containing functional moieties selected from active hydrogen groups or epoxy groups.

34. The curable composition according to claim 33, wherein said composition is a powder coating composition.

35. A process for preparing a prepolymer represented by the formula (IV):

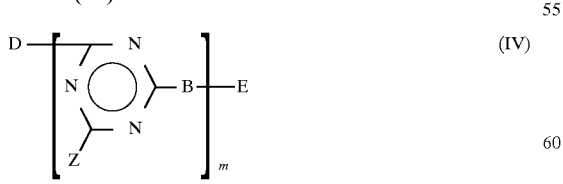 (IV)

wherein

B is a divalent group of a difunctional active hydrogen-containing material;

Z is selected from the group consisting of hydrogen, hydrocarbyl, hydrocarbyloxy, hydrocarbylthio, amido, sulfonamido, hydrocarbylamino, cyclic amino, amino, acyl, halogen and imido represented by

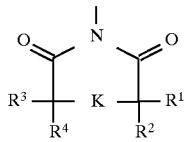

p19 wherein $R^1$, $R^2$, $R^3$ and $R^4$ are independently selected from hydrogen, alkyl having 1 to 12 carbon atoms, alkenyl having 1 to 12 carbon atoms, alkoxy having 1 to 6 carbon atoms, aryl having 6 to 20 carbon atoms or aralkyl having 7 to 20 carbon atoms, and $R^1$ and $R^2$ can form together a methylene or $R^2$ and $R^4$ can form together an aliphatic bridge having up to 6 carbon atoms which may be substituted by one or more alkyl having 1 to 12 carbon atoms, alkoxy having 1 to 6 carbon atoms, aryl having 6 to 20 carbon atoms or aralkyl having 7 to 20 carbon atoms, and K is selected from the group consisting of a single bond, a divalent methylene radical and a double bond, provided that K is only a double bond when $R^2$ and $R^4$ form together an aromatic ring;

D is Z or HB—, wherein Z and B are as previously described; and

E is Z or an imido triazine group represented by

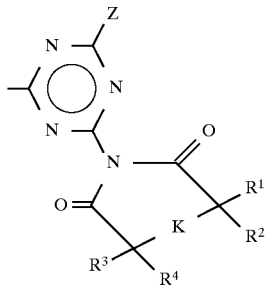

wherein Z, $R^1$, $R^2$ $R^3$, $R^4$ and K are as previously described; and m is from 0 to 100, provided that said prepolymer has at least two pendant imido groups, said process comprising contacting (a) at least one imido functional 1,3,5-triazine represented by the formula

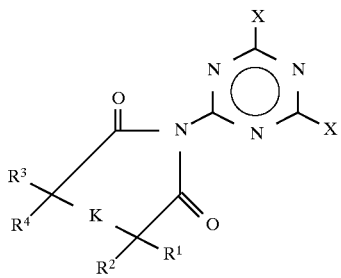

wherein X is selected from the group consisting of hydrogen, hydrocarbyl, hydrocarbyloxy, hydrocarbylthio, amido, sulfonamido, hydrocarbylamino, cyclic amino, amino, acyl, halogen and imido represented by

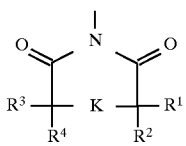

wherein $R^1$, $R^2$, $R^3$, $R^4$ and K are as previously described, provided that at least one X is halogen, and (b) a difunctional active hydrogen-containing material to form the prepolymer.

36. The process according to claim 35, wherein at least one X is chloro.

37. The process according to claim 36, wherein said difunctional active hydrogen-containing material is selected from the group consisting diols and diamines.

38. The process according to claim 37, wherein said at least one imido functional 1,3,5-triazine is a mixture of imido functional 1,3,5-triazines having mono-chloro and bis-chloro functionality.

39. A process for preparing a prepolymer represented by the formula (IV):

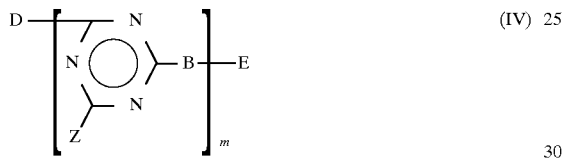

wherein

B is a divalent group of a difunctional active hydrogen-containing material;

Z is selected from the group consisting of hydrogen, hydrocarbyl, hydrocarbyloxy, hydrocarbylthio, amido, sulfonamido, hydrocarbylamino, cyclic amino, amino, acyl, halogen and imido represented by

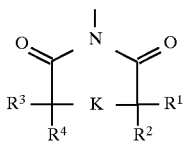

wherein $R^1$, $R^2$, $R^3$ and $R^4$ are independently selected from hydrogen, alkyl having 1 to 12 carbon atoms, alkenyl having 1 to 12 carbon atoms, alkoxy having 1 to 6 carbon atoms, aryl having 6 to 20 carbon atoms or aralkyl having 7 to 20 carbon atoms, and $R^1$ and $R^2$ can form together a methylene or $R^2$ and $R^4$ can form together an aliphatic bridge having up to 6 carbon atoms which may be substituted by one or more alkyl having 1 to 12 carbon atoms, alkoxy having 1 to 6 carbon atoms, aryl having 6 to 20 carbon atoms or aralkyl having 7 to 20 carbon atoms, and K is selected from the group consisting of a single bond, a divalent methylene radical and a double bond, provided that K is only a double bond when $R^2$ and $R^4$ form together an aromatic ring;

D is Z or HB—, wherein Z and B are as previously described; and

E is Z or an imido triazine group represented by

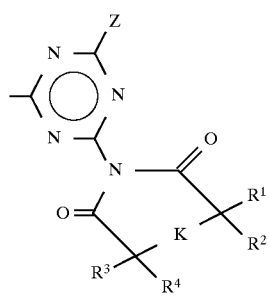

wherein Z, $R^1$, $R^2$ $R^3$, $R^4$ and K are as previously described; and m is from 0 to 100, provided that said prepolymer has at least two pendant imido groups, said process comprising the steps of:

(a) contacting cyanuric halide and a difunctional active hydrogen-containing material to provide a halide functional triazine prepolymer; and (b) contacting said halide functional triazine prepolymer with an imide represented by the formula

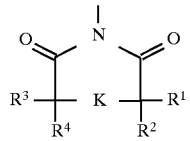

wherein $R^1$, $R^2$, $R^3$, $R^4$ and K are as previously described to provide the prepolymer.

40. The process according to claim 39, wherein said cyanuric halide is cyanuric chloride.

41. The process according to claim 40, wherein said difunctional active hydrogen-containing material is selected from the group consisting of diols and diamines.

* * * * *